United States Patent
Waters

(10) Patent No.: US 9,623,019 B1
(45) Date of Patent: Apr. 18, 2017

(54) TREATMENT OF HYPERANDROGENISM IN WOMEN WITH PAROXETINE AND MYO-INOSITOL

(71) Applicant: Angel May Waters, Windham, ME (US)

(72) Inventor: Angel May Waters, Windham, ME (US)

(*) Notice: Subject to any disclaimer, the term of this patent is extended or adjusted under 35 U.S.C. 154(b) by 0 days.

(21) Appl. No.: 14/959,598

(22) Filed: Dec. 4, 2015

(51) Int. Cl.
*A61K 31/4525* (2006.01)
*A61K 31/047* (2006.01)
*A61K 9/00* (2006.01)

(52) U.S. Cl.
CPC ........ *A61K 31/4525* (2013.01); *A61K 9/0053* (2013.01); *A61K 31/047* (2013.01)

(58) Field of Classification Search
CPC .......................... A61K 31/4525; A61K 31/047
See application file for complete search history.

(56) References Cited

PUBLICATIONS

Bizzarri et al. European Review for Medicinal and Pharmacological Sciences, 2014, vol. 18, pp. 1896-1903.*

* cited by examiner

*Primary Examiner* — James D Anderson

(57) ABSTRACT

The present invention relates to a method of treatment of hyperandrogenism in women with paroxetine and myo-inositol. In women, hyperandrogenism is a hormonal imbalance caused by excess of testosterone and/or reduced estrogen receptor sensitivity. A quantity of paroxetine, and a quantity of myo-insitol are heterogeneously combined together into a medicinal mixture. The medicinal mixture is administered to the patient in order to reduce free testosterone and increase estrogen receptor sensitivity to alleviate symptoms associated with hyperandrogenism without the side effects associated with currently available treatments.

4 Claims, No Drawings

TREATMENT OF HYPERANDROGENISM IN WOMEN WITH PAROXETINE AND MYO-INOSITOL

FIELD OF THE INVENTION

The present invention relates generally to a method for treating female patients suffering from hyperandrogenism. More specifically, the present invention relates to a method for treating a female patient who suffers from excess testosterone and/or reduced estrogen receptor sensitivity.

BACKGROUND OF THE INVENTION

Hyperandrogenism in women is a hormonal imbalance which results in excess testosterone and/or reduced estrogen receptor effects caused by polycystic ovarian syndrome (PCOS), primary functional hyperandrogenism (FAH), congenital adrenal hyperplasia (CAH), aromatase deficiency, ovarian hyperthecosis, adrenal hyperandrogenism (excess adrenal production of DHEA, DHEA sulfate, and androstenedione) and exogenous dehydroepiandrosterone (DHEA) intake. Hyperandrogenism in women causes acne, hirsutism, weight gain, alopecia, irregular menstrual bleeding, insulin resistance, cardiovascular disease, endometrial cancer, and non-alcoholic fatty liver disease.

The most disfiguring effects of hyperandrogenism in women is cystic acne. Scars from cystic acne are left both physically and emotionally. Current treatment for cystic acne caused by hyperandrogenism is exogenous hormones (hormonal contraceptives), oral antibiotics, oral retinoid, and up until just a couple months ago, anti-androgen medications were used. Anti-androgen medications little effect on reducing acne in women, and have side effects that range from hepatotoxicity, carcinogenesis, anemia, heart failure, renal failure, depression, and some are altogether contraindicated in women of childbearing age. Oral retinoid medications have a high propensity for even more devastating side effects to include hepatitis, glomerulonephritis, inflammatory bowel disease, pancreatitis, pseudotumor cerebri, vision impairment, hearing impairment, tinnitus, dyslipidemia, hyperglycemia, depression, psychosis, and aggressive or violent behavior. Both of these treatments have side effects that are dangerous, and they are also less effective than treatment with paroxetine and myo-inositol.

Hormonal contraceptives are typically used, but these medications increase cardiovascular risk, increase risk of breast cancer, weight gain, and can even exacerbate acne. With weight gain there is increased adipose tissue. Increased adipose tissue decreases sex hormone-binding globulin (SHBG) which increases circulating unbound androgens, and makes acne worse. Oral antibiotics are also used; however, oral antibiotics can cause bacterial resistance, hepatic impairment, renal impairment, hearing loss, QT prolongation (the measure of delayed ventricular repolarization), and autoimmune disorders such as Lupus when used for a long period of time.

The present invention reduces the symptoms caused by hyperandrogensim for female patients. The present invention reduces testosterone levels and increasing estrogen and insulin sensitivity, therefore reducing the symptoms cystic acne, hirsutism, weight, alopecia, irregular menstrual bleeding, insulin resistance, dyslipidemia, and non-alcoholic fatty liver disease.

DETAIL DESCRIPTIONS OF THE INVENTION

All illustrations of the drawings are for the purpose of describing selected versions of the present invention and are not intended to limit the scope of the present invention.

The present invention is a method for the treatment of hyperandrogenism in women with paroxetine and myo-inositol. Hyperandrogenism in women is a hormonal imbalance which results in excess testosterone or reduced estrogen receptor effects caused by polycystic ovarian syndrome (PCOS), primary functional hyperandrogenism (FAH), congenital adrenal hyperplasia (CAH), aromatase deficiency, ovarian hyperthecosis, and exogenous dehydroepiandrosterone (DHEA) intake. Hyperandrogenism causes acne, hirsutism, weight gain, alopecia, irregular menstrual bleeding, insulin resistance, cardiovascular disease, endometrial cancer, and non-alcoholic fatty liver disease.

In order to execute the steps of the present invention, the present invention requires a quantity of paroxetine and a quantity myo-insitol. Paroxetine is a selective serotonin reuptake inhibitor which is effective at treatment hyperandrogenism because paroxetine helps the body to endogenously convert the androgens to estrogen, as opposed to taking exogenous hormones by the way of oral contraceptives. Paroxetine is also an estrogen receptor agonist which binds to estrogen receptors to stimulate estrogen-like effects on tissues within the patient's body. As excess testosterone is a potential result of hyperandrogenism, paroxetine treats hyperandrogensim by maintaining a hormonal balance, converting androgens to estrogen. The quantity of paroxetine may be present in anhydrous, hydrous, or crystalline form.

Myo-insitol regulates the patients hormone levels such that supplementation improves several hormonal imbalances by improving ovarian response to endogenous gonadotropins and improves insulin sensitivity. Myo-insitol also has a positive effect on reducing acne, reducing hirsutism, regulating menstrual cycles, and hormonal functions, reducing hyperandrogensim in patients. The quantity of paroxetine and the quantity myo-insitol are administered to a patient daily in order to reduce testosterone levels and increase estrogen receptor sensitivity to alleviate side-effects from hyperandrogenism.

In accordance to the preferred embodiment, the quantity of paroxetine and the quantity of myo-inositol are heterogeneously combined into a medicinal mixture. In accordance to the preferred embodiment of the present invention, the quantity of paroxetine is between 12.5 milligrams and 25 milligrams and the quantity of myo-insitol is between 2 grams and 4 grams. This composition allows for an effective quantity for paroxetine and the quantity of myo-insitol, to be metabolized in order to impart the beneficial properties from each.

Once the medicinal mixture is formed, the medicinal mixture is administered to the patient daily. While the medicinal mixture is able to be administered through a number of methods to the patient, the medicinal mixture is preferred to be administered orally to the patient. Further in accordance to the preferred embodiment, the medicinal mixture is proportioned within a time release capsule in order to allow a portion of the medicinal mixture to be released periodically to be metabolized by the patient. Thus, the duration of the effects of the medicinal mixture is able to be extended. The time release capsule allows for a more constant concentration of the medicinal mixture within the patient's body to prevent hormonal levels from fluctuating greatly. As the medicinal mixture is administered daily, the testosterone levels within the patient's body are constantly regulated by the metabolism of the quantity of paroxetine and the quantity of myo-insitol such that the testosterone level is consistently lower than the testosterone level would be from leaving hyperandrogenism unchecked. Therefore, the side-effects from hyperandrogenism, such as acne, hirsutism, weight gain, alopecia, irregular menstrual bleeding, insulin resistance, cardiovascular disease, endometrial cancer, and non-alcoholic fatty liver disease, are reduced for a patient through the present invention.

Although the invention has been explained in relation to its preferred embodiment, it is to be understood that many other possible modifications and variations can be made without departing from the spirit and scope of the invention as hereinafter claimed.

What is claimed is:

1. A method for treatment of hyperandrogenism in a women comprising the steps of:
   providing a quantity of paroxetine and a quantity of myo-insitol, the quantity of paroxetine being between 12.5 and 25 milligrams, the quantity of myo-insitol being between 2 and 4 grams; and
   administering the quantity of paroxetine and the quantity of myo-insitol to said woman daily.

2. The method of claim 1 further comprising:
   heterogeneously combining the quantity of paroxetine and the quantity of myo-insitol into a medicinal mixture; and
   administering the medicinal mixture said woman daily.

3. The method of claim 2 further comprising:
   the medicinal mixture being administered orally to said woman.

4. The method of claim 2 further comprising:
   providing a time release capsule; and
   proportioning the medicinal mixture within the time release capsule for periodically releasing a portion of the medicinal mixture to be metabolized by said woman.

* * * * *